US005611340A

United States Patent [19]
Souza et al.

[11] Patent Number: 5,611,340
[45] Date of Patent: Mar. 18, 1997

[54] APPARATUS AND METHODS FOR MAGNETIC RESONANCE (MR) ANGIOGRAPHY USING HYDROGEN POLARIZED AT LOW TEMPERATURES

[75] Inventors: Steven P. Souza, Williamstown, Mass.; Charles L. Dumoulin, Ballston Lake, N.Y.

[73] Assignee: General Electric Company, Schenectady, N.Y.

[21] Appl. No.: 537,571

[22] Filed: Oct. 2, 1995

[51] Int. Cl.$^6$ .................................................. A61B 5/055
[52] U.S. Cl. ........................ 128/653.2; 128/654; 324/309
[58] Field of Search ................................. 128/653.2, 654, 128/656, 653.3, 653.4; 324/307, 309

[56] References Cited

U.S. PATENT DOCUMENTS

| | | |
|---|---|---|
| 4,930,510 | 6/1990 | Lindstrom . |
| 5,271,401 | 12/1993 | Fishman . |
| 5,305,751 | 4/1994 | Chopp et al. . |
| 5,357,959 | 10/1994 | Fishman . |
| 5,479,925 | 1/1996 | Dumoulin et al. . |

Primary Examiner—Marvin M. Lateef
Assistant Examiner—Shawna J. Shaw
Attorney, Agent, or Firm—Lawrence P. Zale; Marvin Snyder

[57] ABSTRACT

A magnetic resonance (MR) active invasive device system employs a small, high-field polarizing magnet, and a large low-field magnetic resonance (MR) imaging magnet for the purpose of generating MR angiograms of selected blood vessels. A subject is positioned in a large low-field MR imaging magnet. A catheter is inserted into the patient at or near the root of a vessel tree desired to be imaged. A hydrogen gas is first cooled and condensed into a liquid state, and then passed through the small high-field polarizing magnet where it becomes highly polarized. A contrast fluid is then made by chemically combining the polarized hydrogen with oxygen to obtain highly polarized water. The water is then heated to physiologic temperatures and, if desired, made more physiologically compatible with the addition of substances such as salts. The physiologically conditioned polarized fluid is then introduced into the subject through the catheter. Radiofrequency (RF) pulses and magnetic field gradients are then applied to the patient as in conventional MR imaging. Since the fluid has a larger longitudinal magnetization than tissue which has not passed through the polarizing magnet, the fluid produces a much larger MR response signal than other tissue resulting in the vessel tree being imaged with excellent contrast.

3 Claims, 3 Drawing Sheets

APPARATUS AND METHODS FOR MAGNETIC RESONANCE (MR) ANGIOGRAPHY USING HYDROGEN POLARIZED AT LOW TEMPERATURES

CROSS REFERENCES TO RELATED APPLICATIONS

This application is related to U.S. Patent applications "Magnetic Resonance (MR) Angiography in a low-field imaging magnet" Ser. No. 08/264,283, filed Jun. 23, 1994 by C. Dumoulin, R. Darrow; "MAGNETIC RESONANCE (MR) ANGIOGRAPHY USING A TOROIDAL POLARIZING MAGNET AND A Low-Field Imaging Magnet" by C. Dumoulin and R. Darrow (Ser. No. 08/534,998, filed Sep. 27, 1995); "MAGNETIC RESONANCE (MR) ANGIOGRAPHY USING AN INTEGRATED POLARIZING AND IMAGING MAGNET" by C. Dumoulin and S. Souza (Ser No. 08/537,573, filed Oct. 2, 1995); "APPARATUS AND METHODS FOR MAGNETIC RESONANCE (MR) ANGIOGRAPHY USING FLUIDS POLARIZED AT LOW TEMPERATURES" by C. Dumoulin, S. Souza and R. Darrow (Ser. No. 08/537,572, filed Oct. 2, 1995); "APPARATUS AND METHODS FOR MAGNETIC RESONANCE (MR) IMAGING OF CAVITIES USING FLUIDS POLARIZED AT LOW TEMPERATURES" by S. Souza, C. Dumoulin, R. Darrow and H. Cline (Ser. No. 08/537,574, filed Oct. 2, 1995); and "MAGNETIC RESONANCE (MR) PERFUSION IMAGING in A Low-Field Imaging Magnet" by C. Dumoulin and S. Souza (Ser. No. 08/537,575, filed Oct. 2, 1995); all assigned to the present assignee, and all incorporated by reference.

BACKGROUND OF THE INVENTION

1. Field of the Invention

The present invention relates to medical imaging of blood vessels, and more particularly concerns the use of magnetic resonance to obtain such images.

2. Description of Related Art

Angiography, or the imaging of vascular structures, is very useful in diagnostic and therapeutic medical procedures. MR angiography is performed with a variety of methods, all of which rely on one of two basic phenomena.

The first phenomenon arises from changes in longitudinal spin magnetization as blood moves from one region of the patient to another. Methods that make use of this phenomenon have become known as "in-flow" or "time-of-flight" methods. A commonly used time-of-flight method is three-dimensional time-of-flight angiography. With this method, a region of interest is imaged with a relatively short repetition time, TR, and a relatively strong excitation radio-frequency (RF) pulse. This causes the MR spins within the field-of-view to become saturated and give weak MR response signals. Blood flowing into the field-of-view, however, enters in a fully relaxed state. Consequently, this blood gives a relatively strong MR response signal, until it too becomes saturated. Because of the nature of blood vessel detection with time-of-flight methods, the stationary tissue surrounding the vessel cannot be completely suppressed. In addition, slowly moving blood, and blood that has been in the imaged volume for too long, becomes saturated and is poorly imaged.

A second type of MR angiography is based on the induction of phase shifts in transverse spin magnetization. These phase shifts are directly proportional to velocity and are induced by flow-encoding magnetic field gradient pulses. Phase-sensitive MR angiography methods exploit these phase shifts to create images in which the pixel intensity is a function of blood velocity. While phase-sensitive MR angiography can easily detect slow flow in complicated vessel geometries, it will also detect any moving tissue within the field-of-view. Consequently, phase-sensitive MR angiograms of the heart have artifacts arising from the moving heart muscle and from the moving pools of blood in the heart chambers.

In conventional MR imaging, an inhomogeneity of the static magnetic field produced by the main magnet causes distortion in the image. Therefore a main magnet having homogeneity over a large region is desirable.

Also, a stronger static magnetic field created by the main magnet yields a better signal to noise ratio, all other factors being equal. Typically, the magnets used to create the static magnetic field in an MR scanner have been constructed of a superconducting material requiring very low temperatures, and related support apparatus. This can be very expensive.

Even if a very high field magnet were constructed to maximize the signal-to-noise ratio for MR angiographic imaging, the signal of the surrounding tissue would be increased to the same extent as signals from blood. Consequently, there would be no increase in vessel visibility with the higher magnetic field, all other factors being equal.

Currently, there is a need for a system for obtaining high quality angiography of a selected vessel without the risks of exposure to ionizing radiation and X-ray opaque contrast injections, and without the problems incurred with a large high-field imaging magnet.

SUMMARY OF THE INVENTION

Hydrogen is cooled to cryogenic temperatures to form a liquid. This liquid hydrogen is passed through a polarizing means where it becomes highly polarized. The polarization means includes a high field magnet in which the hydrogen is placed. The hydrogen is made to reside in the polarizing magnetic field for a period longer than several times the longitudinal relaxation time, T1, of hydrogen. After the liquid hydrogen has become highly polarized, it is removed from the polarizing magnet and rapidly heated to physiologic temperatures. It is then combined with oxygen to produce highly-polarized water. Salts or other appropriate materials are added to the highly polarized water to make a solution suitable for injection into a living subject. This polarized fluid is then injected into the patient. MR images are created of the polarized fluid with an MR system which is comprised of radio-frequency and magnetic field gradient coils and a static field imaging magnet. Since the strength of the detected MR signal is determined by the degree of polarization of the injected fluid, which is in turn determined by the strength of the polarizing magnet, and not the strength of the imaging magnet, low-field resistive or permanent imaging magnets may be advantageously used instead of a higher field superconducting magnet.

OBJECTS OF THE INVENTION

It is an object of the present invention to provide a system for imaging selected blood vessels using magnetic resonance without the need for a homogeneous high-field imaging magnet.

It is another object of the present invention to provide a polarization means which can create highly polarized states in aqueous solutions.

It is another object of the present invention to provide a means for the delivery of a highly polarized fluid into a patient.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
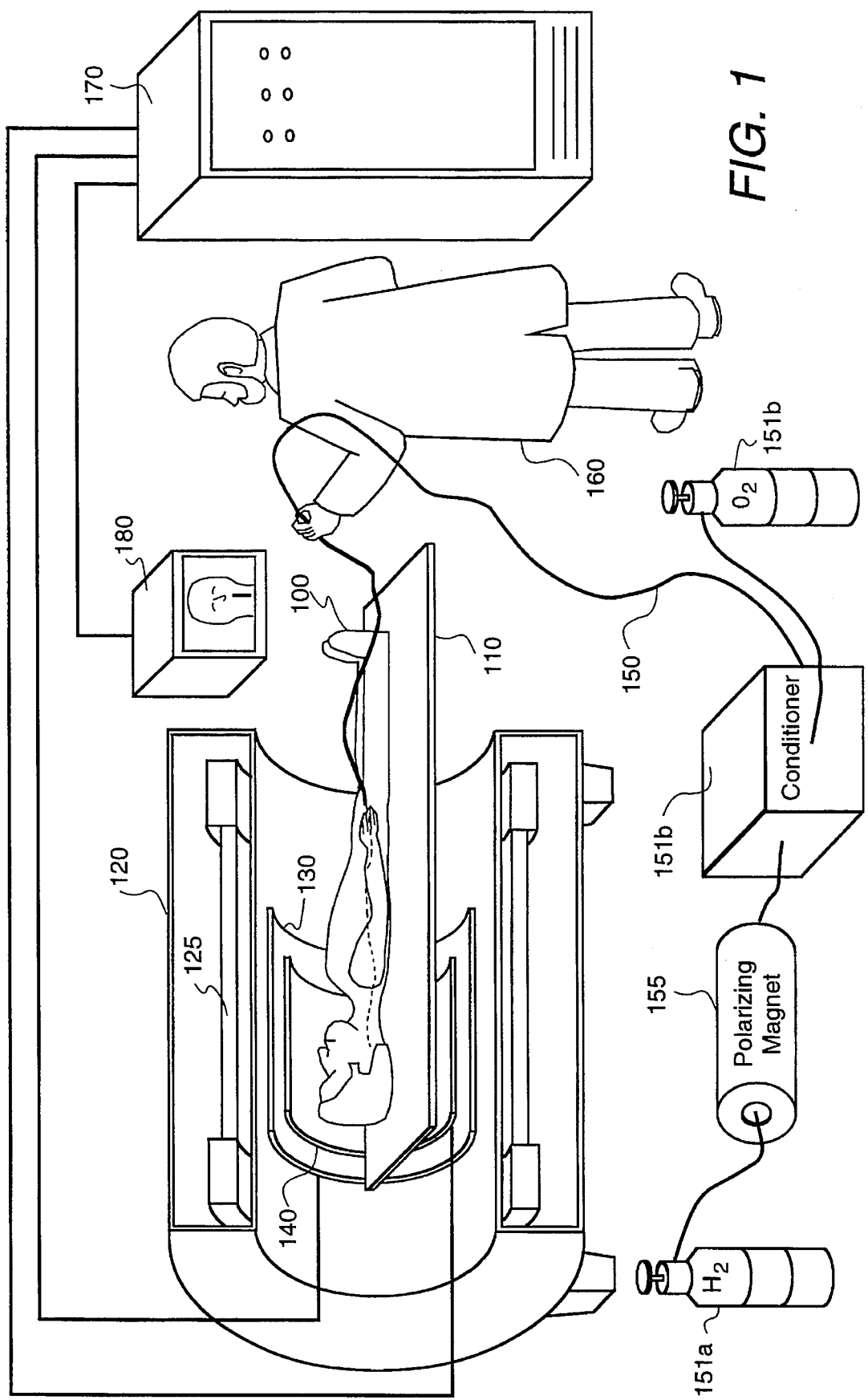
FIG. 1 is a perspective view of a first embodiment of the present invention in operation in which a vessel selective angiogram is being obtained from a subject.

In FIG. 1, a subject 100 is placed on a support table 110 and positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. A region of interest of subject 100 is located in the approximate center of the bore of magnet 125. Subject 100 is surrounded by a set of cylindrical magnetic field gradient coils 130 which create magnetic field gradients of predetermined strength at predetermined times according to predetermined magnetic resonance (MR) pulse sequences, described later. The remaining electronics of the MR imaging system are located in cabinet 170. Gradient coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. RF coil 140 radiates radio-frequency energy into subject 100 at predetermined times and with sufficient power at a predetermined frequency so as to nutate a population of nuclear magnetic spins, hereinafter referred to as 'spins', of subject 100 in a fashion well known to those skilled in the art. RF coil 140, in one embodiment, can also act as a receiver, detecting the MR response signals which are stimulated by nutation, if desired.

The nutation of the spins causes the spins to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

An aqueous solution suitable for injection into subject 100 is created by passing hydrogen gas from a hydrogen gas reservoir 151a to a cryogenic chamber 152 (shown in FIG. 2) where the hydrogen gas is liquefied. Cryogenic chamber 152 is located in a polarizing magnet 155 where the nuclei of the hydrogen molecules become highly polarized.

Polarizing magnet 155 is a superconducting magnet operating with relatively poor homogeneity, but as high a field as practical. Designs in which the field strength reaches 15 Tesla or more are possible. If desired, the magnet can be substantially shielded to prevent stray magnetic fields from disturbing the surrounding environment. This shielding can be accomplished with an active cancellation coil surrounding the internal main coil. Since polarizing magnet 155 is not required to be highly homogeneous, and because of its small size, the magnet should be considerably less expensive than existing MR imaging magnets.

Once the hydrogen in polarizing magnet 155 becomes highly polarized, it is transferred to a physiologic conditioner 153. Transfer of the polarized hydrogen to physiologic conditioner 153 can be performed with a second mechanical transfer means 157 such as a pump, or manually. In physiologic conditioner 153 the hydrogen is reacted with oxygen from an oxygen gas reservoir 151b to form highly polarized water. Physiologic conditioner 153 brings the highly polarized water to approximately body temperature and can add salts or other materials to the fluid to make the fluid more physiologically compatible with subject 100 if desired.

After the fluid has been treated by physiological conditioner 153, the highly polarized fluid is injected through a catheter 150 into subject 100 where it is imaged using conventional MR imaging methods.

The fluid which is injected into the subject 100 through catheter 150 should have the highest amount of polarization possible once it reaches the vessels. Consequently, the polarizing field of polarizing magnet 155 should be high. Also, the hydrogen should be left in the polarizing field for a period of is time greater than five times its longitudinal relaxation time, T1, to reach full magnetization. Once the hydrogen is removed from polarizing magnet 155 it will begin to lose polarization with a half-life of T1. Since the T1 of the cryogenic hydrogen is likely to be long, it may be possible to move the cryogenic hydrogen relatively slowly, or even place it in storage for a selected period of time. As the hydrogen approaches room temperature, however, the T1 will shorten and transfer of the hydrogen to physiological conditioner 153 and then through catheter 150 to subject 100 should be as rapid as possible.

In the current invention additional polarization is obtained by lowering the temperature of the hydrogen. The amount of additional polarization (and hence MR signal) can be derived from the Boltzmann equation:

$$n_e/n_0 = \exp\{(E_e - E_0)/kt\} \quad (1)$$

where $n_e$ is the number of spins in the excited state, $n_0$ is the number of spins in the ground state, $E_e$ is the energy of the excited state, $E_0$ is the energy of the ground state, k is Boltzmann's constant and T is the temperature of the spins. It is useful to note that as the static magnetic field is increased, the energy of the excited state, $E_e$, increases. This results in a decrease in the ratio of the number of spins in the excited state, $n_e$, with respect to the number of spins in the ground state, $n_0$. Since the polarization of an ensemble of spins is directly proportional to the difference in the number of spins in the excited and ground states, stronger static magnetic fields give greater polarization and consequently, are often desirable. It is also useful to note in equation [1] that as the temperature, T, is lowered, the polarization of the spins increases. Consequently, an ensemble of spins which are polarized at low temperature attain a stronger degree of polarization.

Since it is the difference in the number of spins in the ground and excited states which determine the strength of the MR signal, S, it is useful to reformulate Eq. (1) such that:

$$S = C(n_0 n_e) \quad (2)$$

and $$S = C\{n_0\{1 - \exp\{-(E_e - E_0)/kT\}\}\} \quad (3)$$

where C is a constant of proportionality.

Equation 3 can be used to calculate the change in signal intensity expected as the temperature, T, of the spins is changed. For example, if the temperature of the spins is lowered from room temperature to four degrees, Kelvin, Eq. (3) predicts a 66.5 fold increase in signal.

Figure 2:
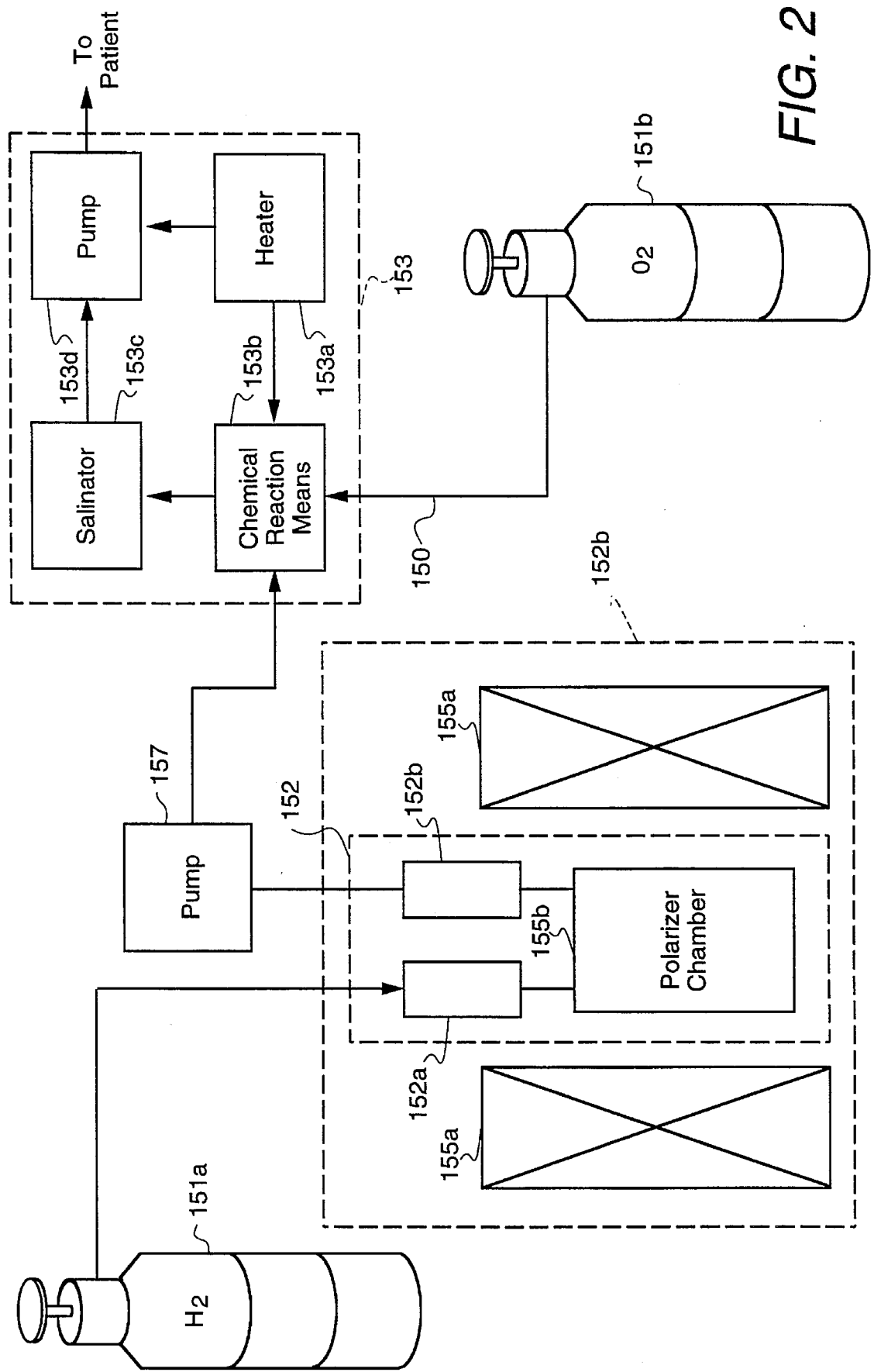
FIG. 2 is a schematic view of one embodiment of a polarization means in which hydrogen is cooled to low temperatures, polarized and then combined with oxygen to produce a solution suitable for injection into a subject.

FIG. 2 is a schematic diagram illustrating the components needed to produce highly polarized fluid suitable for injection into subject 100. Non-polarized hydrogen from hydrogen reservoir 151a is first introduced into cryogenic chamber 152. Cryogenic chamber 152 is comprised of a freezer portion 152a, a polarizing chamber 155b and a warming portion 152b. The net effect of cryogenic chamber 152 on the hydrogen is to contain hydrogen at cryogenic temperatures for a selected time in the polarizing magnetic field of polarizing magnet 155. While in the polarizing magnet, the hydrogen approaches full polarization in an exponential fashion and polarization in excess of 99% of the maximum value can be achieved by allowing the hydrogen to be in polarizing magnet 155 longer than five times the T1 of hydrogen at it current temperature. It should be noted that the T1 of the hydrogen is likely to be relatively long at low temperatures.

After the hydrogen has reached the desired level of polarization, the hydrogen can be removed from polarizing magnet 155 and placed into physiologic conditioner 153. Physiologic conditioner 153 includes a chemical reaction means 153b which chemically combines the polarized hydrogen with oxygen from oxygen supply reservoir 151b. Chemical reaction means 153b can be comprised of a combustion chamber or a fuel cell. The polarized hydrogen entering chemical reaction means 153b and/or the water created in chemical reaction means 153b is heated by a heater 153a which rapidly raises the temperature of the highly-polarized water to provide a highly-polarized liquid which is physiologically compatible with subject 100. Salts can be added to the highly-polarized liquid in a salinator means 153c to enhance the physiological compatibility of the highly-polarized fluid with subject 100. The physiologically compatible highly-polarized liquid is sent to catheter 150 via a pump 153d.

The current invention discloses the formation of cryogenic hydrogen in the liquid state, but other embodiments in which the hydrogen is further cooled to form a solid which is then passed by mechanical means 157, or manually, through polarizing magnet 155 on its way to physiologic conditioner 153 are possible. Other embodiments in which cryogenic chamber 152, polarizing magnet 155 and physiologic conditioner 153 are combined into a single apparatus are also possible.

Once the fluid leaves polarizing magnet 155 it will begin to lose polarization with a half-life equal to its T1. Consequently, it is desirable to deliver the fluid to the patient as quickly as possible. This can be done by minimizing the length of catheter 150 and maximizing the flow velocity.

The imaging system will have the same elements as a conventional MR imaging system, however, they will function somewhat differently. A static magnetic field from a main imaging magnet, shown as 125 in FIGS. 1, 3, should be relatively low (such as 0.1 Tesla) to reduce signals from "stationary" tissue and undesired blood pools contributing to the angiographic image. A small high-field polarization magnet 155 and a large low-field main magnet, instead of a large high-field main magnet may reduce the cost of the system.

Figure 3:
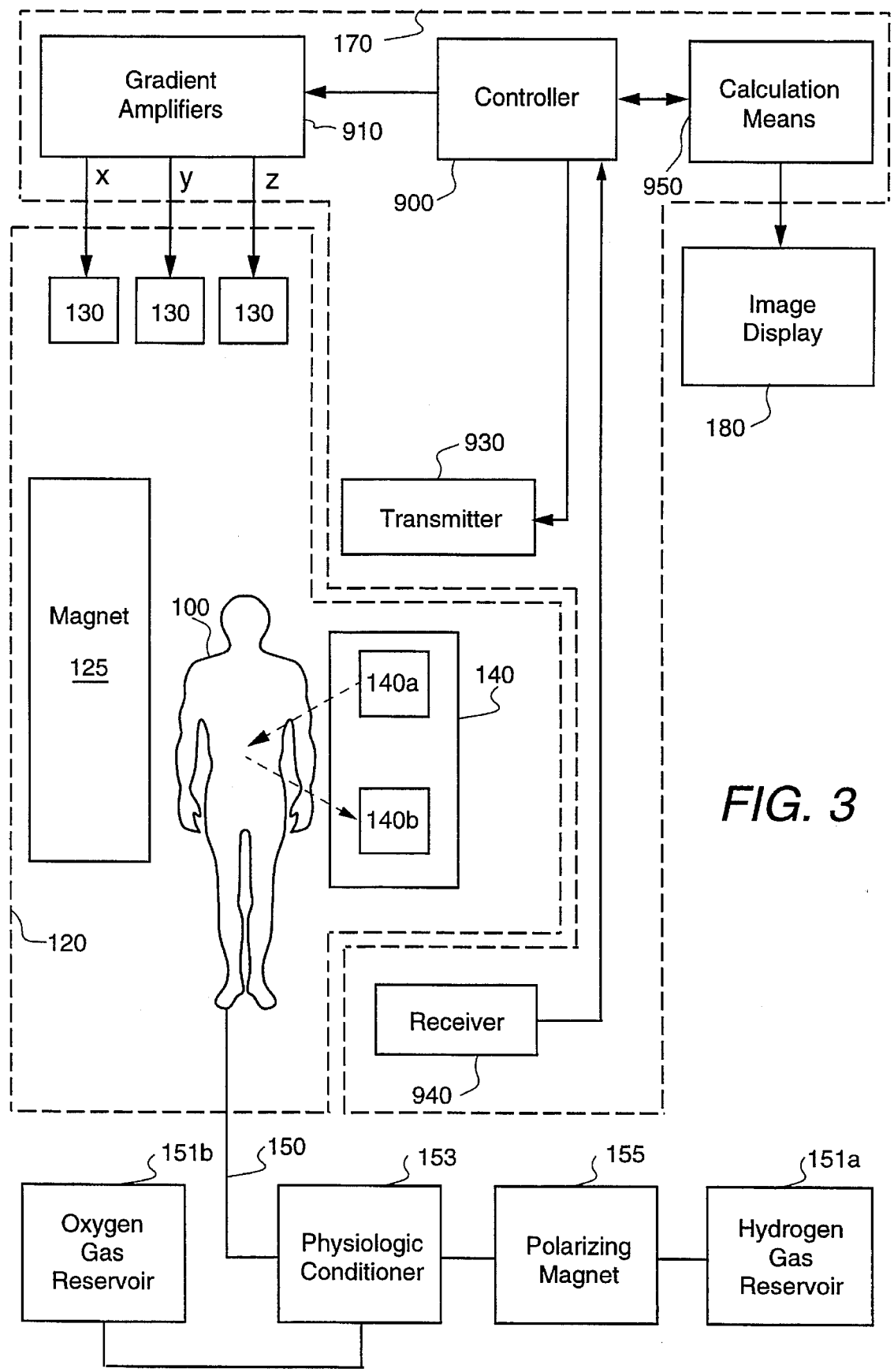
FIG. 3 is a block diagram of a vessel selective MR imaging system suitable for MR angiography according to the present invention.

RF transmitter 930 and RF receiver 940 of the MR system shown in FIG. 3 would be modified to be compatible with the low-field magnet to resonate at a Larmor frequency corresponding to the strength of magnet 125 (e.g., 4.26 MHz in a 0.1 Tesla magnetic field).

In an alternate embodiment, imaging magnet 125 could be an electromagnet which is driven by an amplifier similar to amplifier 910. Such a system should be able to create a pulsed homogeneous field of 30 Gauss (Larmor frequency= 128 kHz). Shielded gradient coil designs meant to reduce the undesirable effects of eddy currents induced in the magnet structure by pulsed gradient fields may be unnecessary with the present invention employing a low-field main magnet 125 (although one may still want them to prevent interference with nearby equipment).

RF transmitter 930, and RF coil 140 of the present invention perform the same functions as an RF subsystem of a conventional MR imaging device. Because the Larmor frequency is very low, however, RF coil designs having resonant frequencies comparable to the Larmor frequency will be required. At these lower frequencies, very little RF transmit power will be required, being a further advantage of the present invention.

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to RF transmitter 930 to generate RF pulses at one or more predetermined frequencies and with suitable power to nutate selected spins within RF coil 140 situated within the bore of magnet 125. Separate RF transmit 140a and receive 140b coils may be employed instead of a single RF transmit and receive coil 140.

MR response signals are sensed by RF coil 140 connected to receiver 940. Since the fluid passing through catheter 150 is comprised, in part, of hydrogen passed through polarizing magnet 155, it acquires a significantly larger longitudinal magnetization, $M_L$, than material which has only been subjected to low-field magnet 125. Consequently, when nutated by the RF pulses, 'spins' which have passed through polarizing magnet 155 exhibit larger transverse magnetization, $M_L$, and consequently produce a much larger MR response signal. Receiver 940 processes the MR response signals by amplifying, demodulating, filtering and digitizing. Controller 900 also collects the signals from receiver 940 and propagates them to a calculation means 950 where they are processed. Calculation means 950 applies a Fourier transformation to the signals received from controller 900 to create an MR image. The image created by calculation means 950 is displayed on an image display means 180.

The signal-to-noise ratio and contrast of signals from subject 100 can be estimated for an embodiment of the present invention in which a 0.1 Tesla imaging magnet is used with a 10.0 Tesla polarizing magnet and a cryogenic pellet former operating at 4 degrees Kelvin. The MR response signal of 'spins' in subject 100 which did not pass through polarizing magnet 155 experience a 0.1T magnetic field. Spins that pass through the 10T polarizing magnet, however, will have a polarization which is 100 times stronger. Hydrogen polarized at 4 degrees Kelvin have an additional factor of 66.5 in polarization. Therefore, the MR signal difference, or contrast, between polarized and non-polarized 'spins' would be a factor of 6,650. Note that in a conventional imaging system which does not use any enhanced polarization means, the ratio of signal intensity in the blood vessels and surrounding tissue is approximately 1 and rarely greater than 2.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

It should also be noted that the technique described here could be used with chemical substances other than hydrogen and oxygen to give polarized substances which can be used for magnetic resonance imaging of hydrogen or other magnetic resonance active nuclei.

While several presently preferred embodiments of the novel MR vascular imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) imaging system for obtaining vessel-selective MR angiographic images from a subject comprising:

a) an imaging magnet for applying a substantially uniform magnetic field over said subject;
    b) a hydrogen supply;
    c) an oxygen supply;
    d) a cryogenic cooling means for receiving and cooling a selected portion of hydrogen from the hydrogen supply;
    e) a high-field polarizing magnet for polarizing the cooled hydrogen;
    f) a chemical reaction means for combining the polarized hydrogen with oxygen from the oxygen supply to form polarized water;
    g) a physiologic conditioner means for heating the polarized water substantially to a temperature suitable for injection into said subject, and for adding solutes to create a polarized contrast fluid having a chemical composition suitable for injection into said subject;
    h) a catheter for routing the polarized contrast fluid from the physiologic conditioner means into said subject;
    i) an RF transmitter means for transmitting RF energy into said subject of a selected duration, amplitude and frequency to cause nutation of the contrast fluid and other tissue within said subject;
    j) a gradient means for varying the amplitude of the magnetic field in at least one spatial dimension over time;
    k) an RF receive coil for detecting a set of MR response signals from the contrast fluid and other tissue within said subject;
    l) a receiver means coupled to the RF receive coil for receiving the detected MR response signals;
    m) a calculation means for calculating an image from the detected MR response signals;
    n) a controller means connected to the RF transmitter means, the receiver means, the calculation means and the gradient means, for activating the RF transmitter means, the receiver means, the calculation means and the gradient means each according to a predetermined MR pulse sequence; and
    o) a display means connected to the calculation means for displaying the calculated image to an operator.

2. A method of obtaining magnetic resonance (MR) angiographic images from a subject comprising:

a) applying a substantially homogeneous magnetic field over said subject;
    b) cooling a selected portion of hydrogen;
    c) polarizing the selected portion of hydrogen by passing it through a high-field polarizing magnet;
    d) combining the polarized hydrogen with oxygen to obtain polarized water;
    e) adding chemical solutes to the polarized water to create a polarized contrast fluid with a chemical composition which may safely be injected into said subject;
    f) routing the polarized contrast fluid into a selected vessel of said subject;
    g) transmitting RF energy into said subject of a selected duration, amplitude and frequency to cause nutation of the contrast fluid and other tissue within said subject;
    h) varying the amplitude of the magnetic field in at least one spatial dimension over time;
    i) detecting a set of MR response signals from the polarized contrast fluid and other tissue within said subject;
    j) receiving the detected MR response signals;
    k) calculating an image from the detected MR response signals; and
    l) displaying the calculated image to an operator.

3. The method of obtaining magnetic resonance (MR) angiographic images of claim 2 wherein the selected portion of hydrogen is passed through the polarizing magnet in the absence of a radiofrequency (RF) excitation pulse.

* * * * *